United States Patent
Lecue et al.

(10) Patent No.: US 10,824,663 B2
(45) Date of Patent: Nov. 3, 2020

(54) ADVERSE INFORMATION BASED ONTOLOGY REINFORCEMENT

(71) Applicant: ACCENTURE GLOBAL SOLUTIONS LIMITED, Dublin (IE)

(72) Inventors: Freddy Lecue, Dublin (IE); Md Faisal Zaman, Dublin (IE)

(73) Assignee: ACCENTURE GLOBAL SOLUTIONS LIMITED, Dublin (IE)

( * ) Notice: Subject to any disclaimer, the term of this patent is extended or adjusted under 35 U.S.C. 154(b) by 331 days.

(21) Appl. No.: 15/922,619

(22) Filed: Mar. 15, 2018

(65) Prior Publication Data

US 2019/0286743 A1    Sep. 19, 2019

(51) Int. Cl.
*G06F 17/00* (2019.01)
*G06F 16/36* (2019.01)
*G16H 70/40* (2018.01)
*G06F 16/335* (2019.01)

(52) U.S. Cl.
CPC .......... *G06F 16/367* (2019.01); *G06F 16/335* (2019.01); *G16H 70/40* (2018.01)

(58) Field of Classification Search
CPC ............... G06F 40/284; G06F 19/3418; G06F 19/3481; G06F 40/205; G06F 40/211; G06F 40/253
See application file for complete search history.

(56) References Cited

U.S. PATENT DOCUMENTS

2013/0096946 A1*   4/2013   Shah ..................... G06Q 50/24
                                                                      705/3

* cited by examiner

*Primary Examiner* — Truong V Vo
(74) *Attorney, Agent, or Firm* — Mannava & Kang, P.C.

(57) ABSTRACT

According to an example, with respect to adverse information based ontology reinforcement, adverse information related to a product or a process may be ascertained and analyzed to further identify and ascertain a relevant ontology of a plurality of ontologies. A determination may be made as to whether the adverse information is present in the ascertained ontology, and if not, the adverse information may be integrated into the ascertained ontology to generate an updated ontology. Similar existing information corresponding to the ascertained adverse information may be identified in the updated ontology to determine an inconsistency between the identified similar existing information and the ascertained adverse information. The determined inconsistency may be used to modify the updated ontology to generate a reinforced ontology.

19 Claims, 12 Drawing Sheets

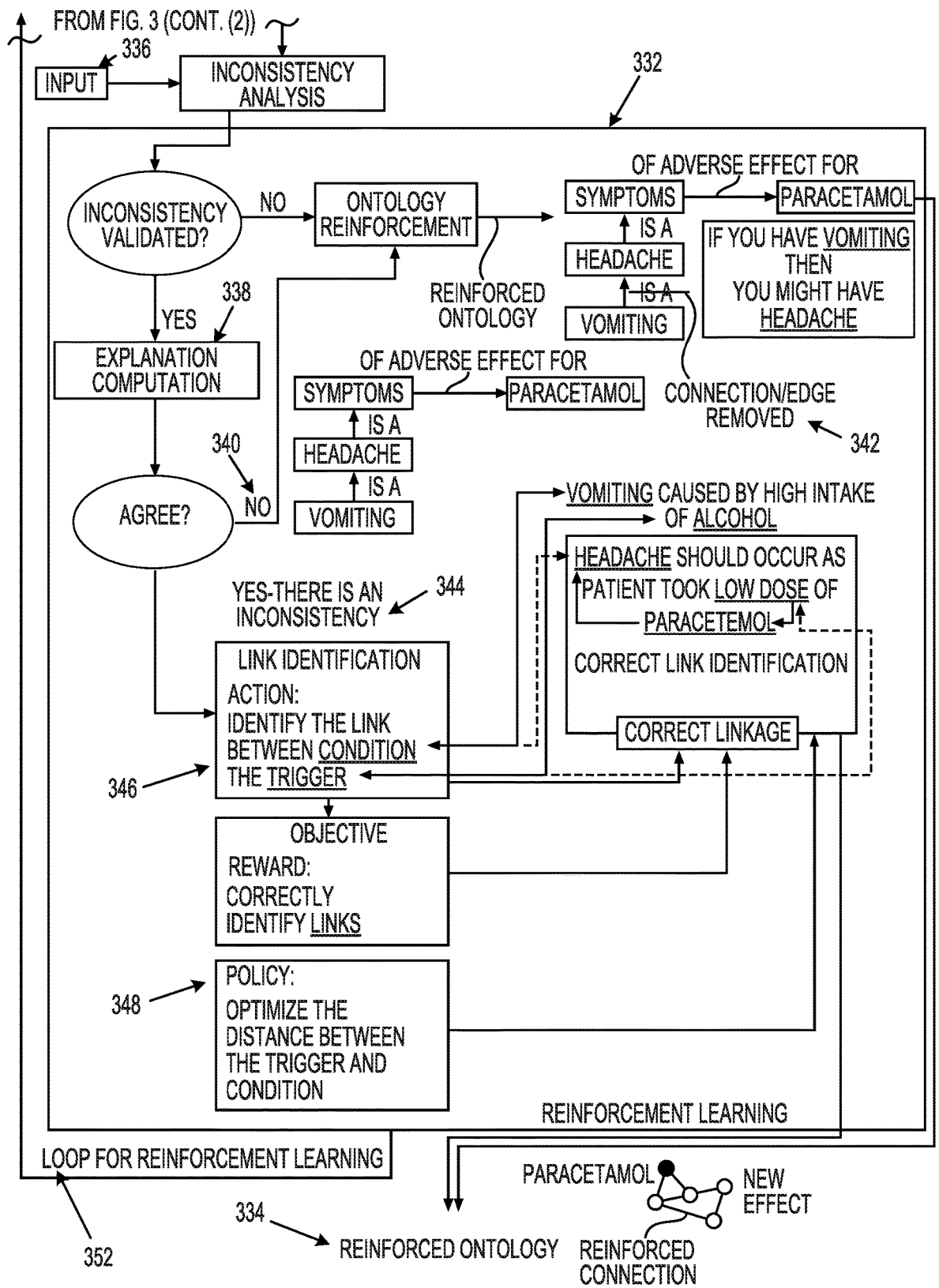
FIG. 3 (Cont. (2))

500

```
┌─────────────────────────────────────────────────────────┐
│  ANALYZE ADVERSE INFORMATION RELATED TO A PRODUCT OR A  │
│                        PROCESS                          │
│                          502                            │
└─────────────────────────────────────────────────────────┘
                              │
                              ▼
┌─────────────────────────────────────────────────────────┐
│  IDENTIFY, BASED ON THE ADVERSE INFORMATION RELATED TO  │
│  THE PRODUCT OR THE PROCESS, A RELEVANT ONTOLOGY OF A   │
│                  PLURALITY OF ONTOLOGIES                │
│                          504                            │
└─────────────────────────────────────────────────────────┘
                              │
                              ▼
┌─────────────────────────────────────────────────────────┐
│  ASCERTAIN, OVER A NETWORK, THE RELEVANT ONTOLOGY OF    │
│              THE PLURALITY OF ONTOLOGIES                │
│                          506                            │
└─────────────────────────────────────────────────────────┘
                              │
                              ▼
┌─────────────────────────────────────────────────────────┐
│  DETERMINE WHETHER THE ADVERSE INFORMATION IS PRESENT   │
│               IN THE ASCERTAINED ONTOLOGY               │
│                          508                            │
└─────────────────────────────────────────────────────────┘
                              │
                              ▼
┌─────────────────────────────────────────────────────────┐
│  BASED ON A DETERMINATION THAT THE ADVERSE INFORMATION  │
│  IS PRESENT IN THE ASCERTAINED ONTOLOGY, MERGE THE      │
│  ADVERSE INFORMATION INTO THE ASCERTAINED ONTOLOGY WITH │
│  SIMILAR INFORMATION PRESENT IN THE ASCERTAINED         │
│  ONTOLOGY                                               │
│                          510                            │
└─────────────────────────────────────────────────────────┘
                              │
                              ▼
                            ( A )
```

```
BASED ON A DETERMINATION THAT THE ADVERSE INFORMATION IS
NOT PRESENT IN THE ASCERTAINED ONTOLOGY, ADD THE ADVERSE
INFORMATION INTO THE ASCERTAINED ONTOLOGY AS NEW
INFORMATION
512
```

```
GENERATE, BASED ON THE MERGED OR ADDED ADVERSE
INFORMATION, AN UPDATED ONTOLOGY
514
```

```
IDENTIFY, IN THE UPDATED ONTOLOGY, SIMILAR EXISTING
INFORMATION CORRESPONDING TO THE ASCERTAINED ADVERSE
INFORMATION
516
```

```
DETERMINE, BASED ON AN ANALYSIS OF THE IDENTIFIED SIMILAR
EXISTING INFORMATION AND THE ASCERTAINED ADVERSE
INFORMATION, AN INCONSISTENCY BETWEEN THE IDENTIFIED
SIMILAR EXISTING INFORMATION AND THE ASCERTAINED ADVERSE
INFORMATION
518
```

```
MODIFY, BASED ON THE DETERMINED INCONSISTENCY BETWEEN
THE IDENTIFIED SIMILAR EXISTING INFORMATION AND THE
ASCERTAINED ADVERSE INFORMATION, THE UPDATED ONTOLOGY TO
GENERATE A REINFORCED ONTOLOGY
520
```

*FIG. 5*
*(CONT.)*

ADVERSE INFORMATION BASED ONTOLOGY REINFORCEMENT

BACKGROUND

An ontology may be described as a set of entities and the relationships between the entities. In a similar manner, a type of ontology may include a knowledge graph that may be described as data points that are specified as nodes, and relationships between the data points that are specified as edges. An example of an ontology includes a medical drug ontology that includes causes and adverse effects related to a medical drug.

BRIEF DESCRIPTION OF DRAWINGS

Features of the present disclosure are illustrated by way of examples shown in the following figures. In the following figures, like numerals indicate like elements, in which

FIG. 5 illustrates a flowchart of a method for adverse information based ontology reinforcement, according to an example of the present disclosure.

DETAILED DESCRIPTION

Figure 1:
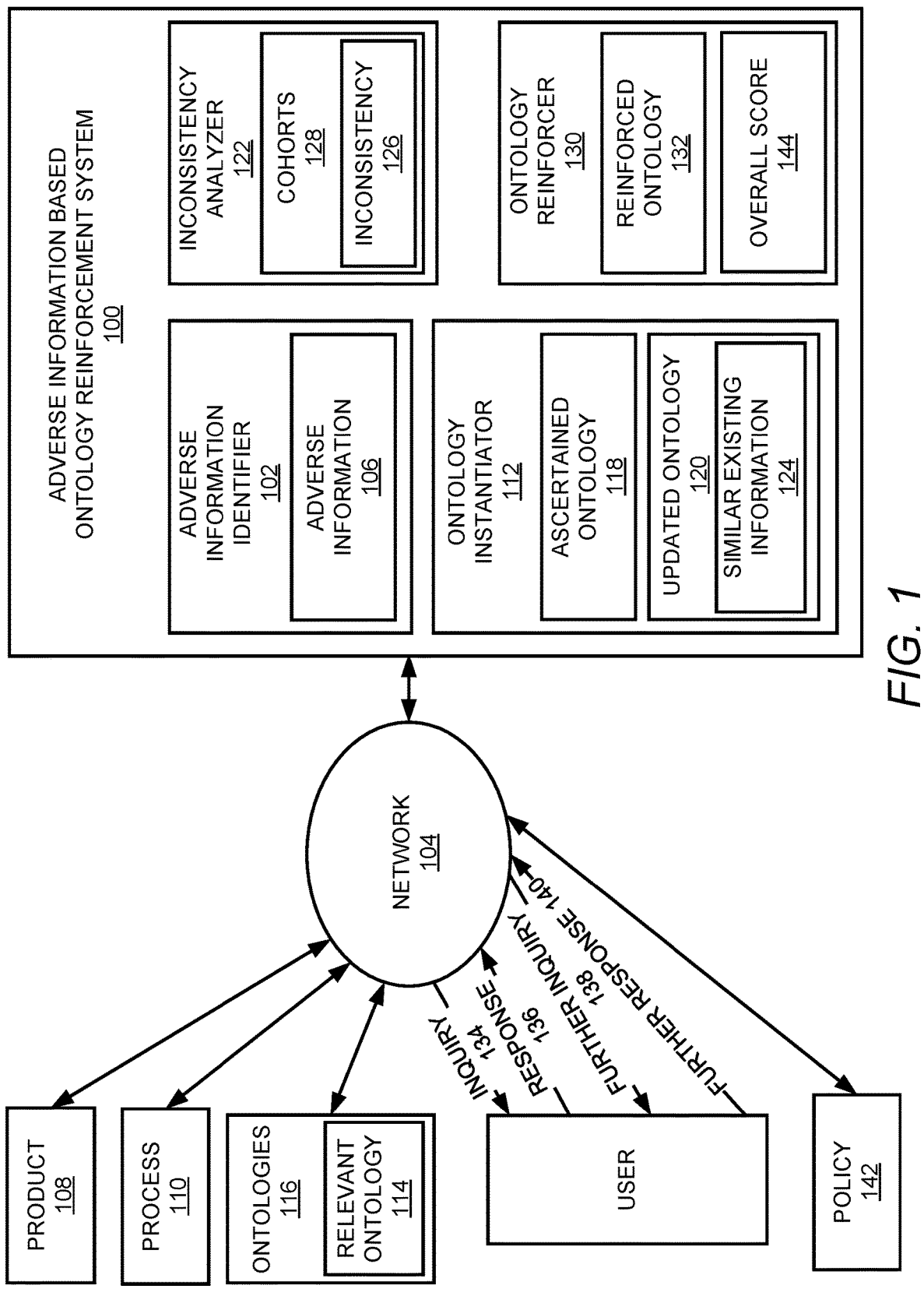
FIG. 1 illustrates an architecture of an adverse information based ontology reinforcement system, according to an example of the present disclosure.

For simplicity and illustrative purposes, the present disclosure is described by referring mainly to examples thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure.

Throughout the present disclosure, the terms "a" and "an" are intended to denote at least one of a particular element. As used herein, the term "includes" means includes but not limited to, the term "including" means including but not limited to. The term "based on" means based at least in part on.

Adverse information based ontology reinforcement systems, methods for adverse information based ontology reinforcement, and non-transitory computer readable media having stored thereon machine readable instructions for adverse information based ontology reinforcement are disclosed herein. The systems, methods, and non-transitory computer readable media disclosed herein provide for analysis of a relevant ontology, and an output, based on the analysis, that includes a reinforced ontology with reinforced connections that may include removed and/or new connections, thus minimizing inconsistencies in an ontology. By reinforcing the ontology, the scope and/or focus of the ontology may be changed to thus focus on the most important parts of the relevant ontology.

With respect to ontology reinforcement, a virtually indefinite number of ontologies may exist with respect to various technological and non-technological areas. For example, ontologies may exist with respect to areas such as medicines, treatments, electronics, mechanics, etc. For each of these areas, ontologies may exist with respect to different types sub-areas, such as dosages of medicines, types of treatments, types of electronics, etc. For ontologies that may include hundreds or thousands of entities and the relationships between the entities, it is technically challenging to objectively ascertain and modify changes to such relationships. It is also technically challenging to objectively ascertain and remove errors in ontologies.

In order to address at least the aforementioned technical challenges with respect to objective modification of changes to relationships between entities in an ontology, the systems, methods, and non-transitory computer readable media disclosed herein provide an adverse information identifier that is executed by at least one hardware processor to ascertain, over a network, adverse information related to a product or a process. An ontology instantiator that is executed by the at least one hardware processor may analyze the adverse information related to the product or the process, and identify, based on the adverse information related to the product or the process, a relevant ontology of a plurality of ontologies. The ontology instantiator may ascertain, over the network, the relevant ontology of the plurality of ontologies. The relevant ontology may be designated an ascertained ontology. The ontology instantiator may determine whether the adverse information is present in the ascertained ontology. Based on a determination that the adverse information is not present in the ascertained ontology, the ontology instantiator may integrate the adverse information into the ascertained ontology.

The ontology instantiator may generate, based on the integrated adverse information, an updated ontology. An inconsistency analyzer that is executed by the at least one hardware processor may identify, in the updated ontology, similar existing information corresponding to the ascertained adverse information, and determine, based on an analysis of the identified similar existing information and the ascertained adverse information, an inconsistency between the identified similar existing information and the ascertained adverse information. An ontology reinforcer that is executed by the at least one hardware processor may modify, based on the determined inconsistency between the identified similar existing information and the ascertained adverse information, the updated ontology to generate a reinforced ontology.

The systems, methods, and non-transitory computer readable media disclosed herein thus provide technical benefits of objective modification of changes to relationships between entities in an ontology. In this regard, the systems, methods, and non-transitory computer readable media disclosed herein provide for automation (e.g., without human intervention) of the processes by which ontologies are analyzed and updated. Removal of errors in ontologies also provide for technical benefits such as reduced processing and related computer usage with respect to inquiries to such ontologies. For example, any inconsistencies in an ontology may be removed to thus provide for reduced processing and related computer resource utilization as inquiries to such inconsistent relationships may be eliminated. Thus, by removing inconsistencies in an ontology, the ontology may be reinforced to focus on the most relevant parts of the ontology, which may be initially triggered by the inconsistencies. In this regard, the reinforced ontology may provide technical benefits such as reduced processing and related computer usage with respect to inquiries to such ontologies, and reduced network bandwidth consumption between a device, such as a medical diagnosis device that may utilize a reinforced ontology, such as a reinforced medical ontology for medically related inquiries. Thus, for an example of the medical diagnosis device, the operation of the medical diagnosis device may be improved to reduce erroneous results that may be generated based on inquiries to the reinforced medical ontology. Operations of other devices that may inquire a reinforced ontology may be similarly improved based on the reduction of inconsistent ontology content.

In some examples, elements of the adverse information based ontology reinforcement system may be machine readable instructions stored on a non-transitory computer readable medium. In this regard, the adverse information based ontology reinforcement system may include or be a non-transitory computer readable medium. In some examples, the elements of the adverse information based ontology reinforcement system may be hardware or a combination of machine readable instructions and hardware.

FIG. 1 illustrates an architecture of an adverse information based ontology reinforcement system 100 (hereinafter "system 100"), according to an example of the present disclosure.

Referring to FIG. 1, the system 100 may include an adverse information identifier 102 that is executed by at least one hardware processor (e.g., the hardware processor 402 of FIG. 4, and/or the hardware processor 604 of FIG. 6) to ascertain, over a network 104, adverse information 106 related to a product 108 or a process 110.

According to examples, the adverse information 106 may include an adverse effect related to a product that includes a medical drug. According to other examples, the adverse information 106 may be related to any manufacturing, food, information technology, etc., products that include descriptive information. For example, in the context of food, most food companies provide allergies related information. In this regard, an ontology may include new regulations requiring information related to trials. In such a case, some products may be at risk for some populations, and that might change over time. The adverse information 106 may therefore be related to such changes to products over time.

An ontology instantiator 112 that is executed the by at least one hardware processor (e.g., the hardware processor 402 of FIG. 4, and/or the hardware processor 604 of FIG. 6) may analyze the adverse information 106 related to the product 108 or the process 110. The ontology instantiator 112 may identify, based on the adverse information 106 related to the product 108 or the process 110, a relevant ontology 114 of a plurality of ontologies 116. The ontology instantiator 112 may ascertain, over the network 104, the relevant ontology 114 of the plurality of ontologies 116. In this regard, the ontology instantiator 112 may receive the plurality of ontologies 116 from which the relevant ontology 114 is identified. The relevant ontology 114 may be designated an ascertained ontology 118.

The ontology instantiator 112 may determine whether the adverse information 106 is present in the ascertained ontology 118.

Based on a determination that the adverse information 106 is not present in the ascertained ontology 118, the ontology instantiator 112 may integrate the adverse information 106 into the ascertained ontology 118. Further, the ontology instantiator 112 may generate, based on the integrated adverse information, an updated ontology 120.

According to examples, the ontology instantiator 112 may integrate the adverse information 106 into the ascertained ontology 118 by adding the adverse information 106 into the ascertained ontology 118 as new information.

Based on a determination that the adverse information 106 is present in the ascertained ontology 118, the ontology instantiator 112 may merge the adverse information 106 into the ascertained ontology 118 with similar information present in the ascertained ontology 118.

An inconsistency analyzer 122 that is executed by the at least one hardware processor (e.g., the hardware processor 402 of FIG. 4, and/or the hardware processor 604 of FIG. 6) may identify, in the updated ontology 120, similar existing information 124 corresponding to the ascertained adverse information 106. Further, the inconsistency analyzer 122 may determine, based on an analysis of the identified similar existing information 124 and the ascertained adverse information 106, an inconsistency 126 between the identified similar existing information 124 and the ascertained adverse information 106.

According to examples, the inconsistency analyzer 122 may determine, based on the analysis of the identified similar existing information 124 and the ascertained adverse information 106, the inconsistency 126 between the identified similar existing information 124 and the ascertained adverse information 106 by identifying, based on the identified similar existing information 124 and the ascertained adverse information 106, cohorts 128 that are affected by the product 108 or the process 110 related to the ascertained adverse information 106. In this regard, the inconsistency analyzer 122 may determine, based on the identified cohorts 128, a pair of cohorts that are inconsistent with each other. Further, the inconsistency analyzer 122 may determine, based on the pair of cohorts that are inconsistent with each other, whether the inconsistency 126 exists between the identified similar existing information 124 and the ascertained adverse information 106. Further, based on a determination that the inconsistency 126 exists between the identified similar existing information 124 and the ascertained adverse information 106, the inconsistency analyzer 122 may identify a root cause of the determined inconsistency 126.

An ontology reinforcer 130 that is executed by the at least one hardware processor (e.g., the hardware processor 402 of FIG. 4, and/or the hardware processor 604 of FIG. 6) may modify, based on the determined inconsistency 126 between the identified similar existing information 124 and the ascertained adverse information 106, the updated ontology 120 to generate a reinforced ontology 132.

According to examples, the ontology reinforcer 130 may further generate an output that includes the reinforced ontology 132. Further, the ontology reinforcer 130 may transmit, over the network 104, the reinforced ontology 132 for storage in a database that includes the plurality of ontologies 116. In this regard, the reinforced ontology 132 may be utilized for further analysis related to the product 108 or the process 110.

According to examples, the ontology reinforcer 130 may modify, based on the determined inconsistency 126 between the identified similar existing information 124 and the ascertained adverse information 106, the updated ontology 120 to generate the reinforced ontology 132 by generating an inquiry 134 that includes the determined inconsistency 126. The ontology reinforcer 130 may receive, based on the inquiry 134, a response 136 that includes a confirmation of whether the determined inconsistency 126 is correct or incorrect. Based on the confirmation that the determined inconsistency 126 is incorrect, the ontology reinforcer 130 may remove the determined inconsistency 126 between the identified similar existing information 124 and the ascertained adverse information 106 to generate the reinforced ontology 132.

According to examples, based on the confirmation that the determined inconsistency 126 is correct, the ontology reinforcer 130 may generate a further inquiry 138 that includes an explanation for the determined inconsistency. The ontology reinforcer 130 may receive, based on the further inquiry 138, a further response 140 that includes a further confirmation of disagreement with the explanation for the determined inconsistency 126. Based on the further confirmation of the disagreement with the explanation for the determined inconsistency 126, the ontology reinforcer 130 may remove the determined inconsistency 126 between the identified similar existing information 124 and the ascertained adverse information 106 to generate the reinforced ontology 132.

According to examples, the ontology reinforcer 130 may receive, based on the further inquiry 138, the further response 140 that includes a further confirmation of agreement with the explanation for the determined inconsistency 126. Based on the further confirmation of the agreement with the explanation for the determined inconsistency 126, the ontology reinforcer 130 may generate the reinforced ontology 132. In this regard, the ontology reinforcer 130 may ascertain, for the updated ontology 120, a link between a condition and a trigger related to the determined inconsistency 126. The ontology reinforcer 130 may ascertain a policy 142 that is used to correct the link. The ontology reinforcer 130 may assign a weight to each link of the updated ontology 120 according to the ascertained policy 142. The ontology reinforcer 130 may determine, based on the assigned weight to each link of the updated ontology 120 according to the ascertained policy 142, the reinforced ontology 132. In this regard, the ontology reinforcer 130 may identify a path between nodes associated with the determined inconsistency 126, where the path includes a plurality of links. The ontology reinforcer 130 may select, from the path, a link for removal based on the ascertained policy 142. The ontology reinforcer 130 may utilize the assigned weight for each link to determine an overall score 144 based on the removal of the selected link. The ontology reinforcer 130 may determine whether the removal of the selected link results in a lowest overall score compared to removal of another link of the path. Based on a determination that the removal of the selected link results in the lowest overall score, the ontology reinforcer 130 may remove the selected link. Further, the ontology reinforcer 130 may determine the reinforced ontology 132 by removing the determined inconsistency 126 based on the removal of the selected link that results in the lowest overall score.

According to examples, the ascertained policy 142 may include removal of a link closest to one of the nodes.

Figure 2:
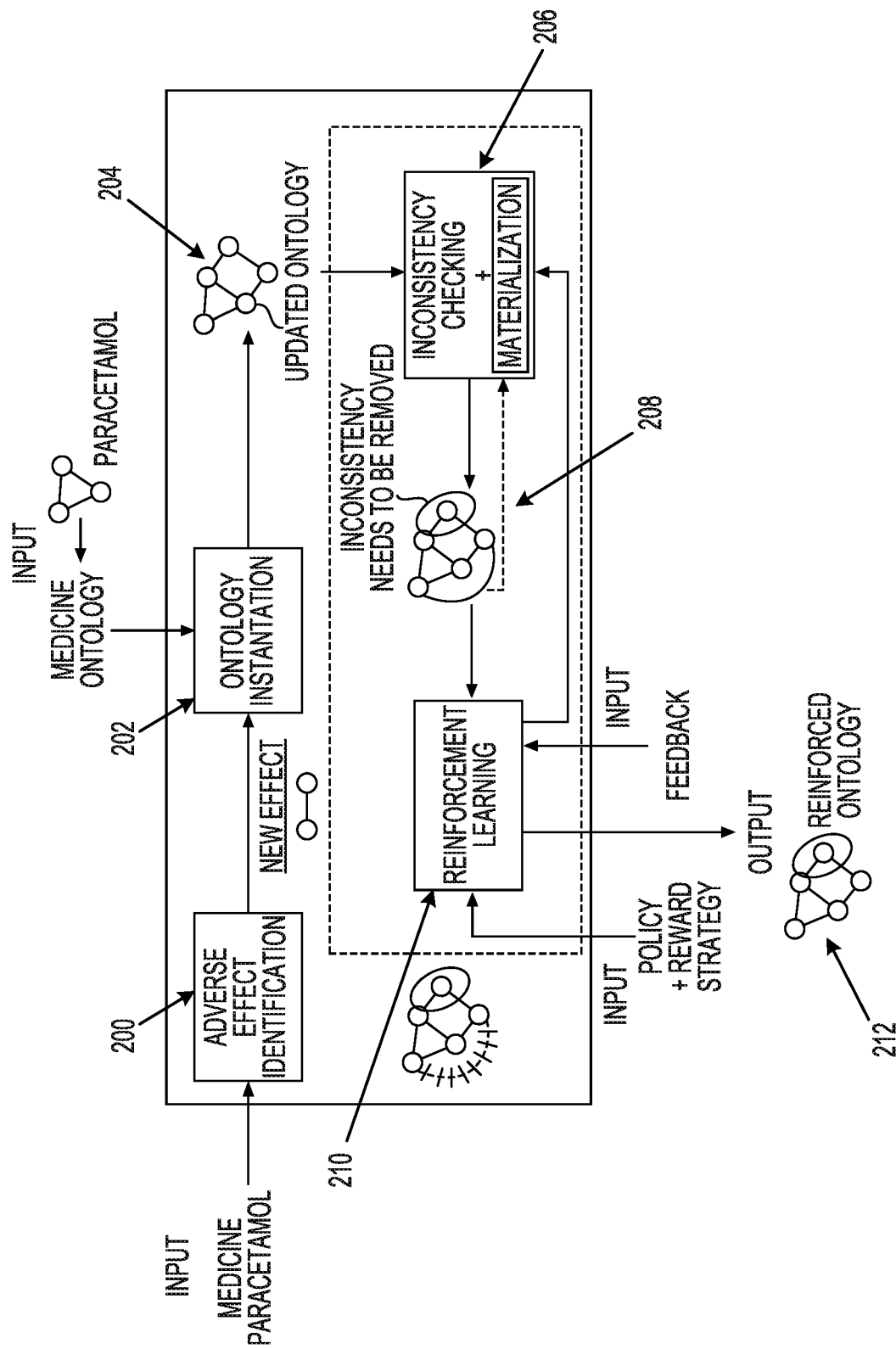
FIG. 2 illustrates further details of the architecture of the adverse information based ontology reinforcement system of FIG. 1, and operation of the adverse information based ontology reinforcement system of FIG. 1 with respect to a medical ontology, according to an example of the present disclosure.

FIG. 2 illustrates further details of the architecture of the system 100, and operation of the system 100 with respect to a medical ontology, according to an example of the present disclosure.

Referring to FIG. 2, at 200, the ontology instantiator 112 may analyze the adverse information 106 related to the product 108 or the process 110. For the example of FIG. 2, the product 108 may include a medicine, and specifically, a paracetamol. The adverse information 106 may be noted as a "new effect" for the example of FIG. 2.

At 202, the ontology instantiator 112 may identify, based on the adverse information 106 related to the product 108, a relevant ontology 114 of a plurality of ontologies 116. The ontology instantiator 112 may ascertain, over the network 104, the relevant ontology 114 of the plurality of ontologies 116. The relevant ontology 114 may be designated an ascertained ontology 118. For the example of FIG. 2, the ascertained ontology 118 may be designated as a "medicine ontology", and specifically, a paracetamol ontology.

The ontology instantiator 112 may determine whether the adverse information 106 is present in the ascertained ontology 118.

Based on a determination that the adverse information 106 is not present in the ascertained ontology 118, the ontology instantiator 112 may integrate the adverse information 106 into the ascertained ontology 118. Further, the ontology instantiator 112 may generate, based on the integrated adverse information, an updated ontology 120 as shown at 204.

Based on a determination that the adverse information 106 is present in the ascertained ontology 118, the ontology instantiator 112 may merge the adverse information 106 into the ascertained ontology 118 with similar information present in the ascertained ontology 118.

At 206, the inconsistency analyzer 122 may identify, in the updated ontology 120, similar existing information 124 corresponding to the ascertained adverse information 106. Further, at 208, the inconsistency analyzer 122 may determine, based on an analysis of the identified similar existing information 124 and the ascertained adverse information 106, the inconsistency 126 between the identified similar existing information 124 and the ascertained adverse information 106.

At 210, the ontology reinforcer 130 may modify, based on the determined inconsistency 126 between the identified similar existing information 124 and the ascertained adverse information 106, the updated ontology 120 to generate, at 212, the reinforced ontology 132.

Figure 3:
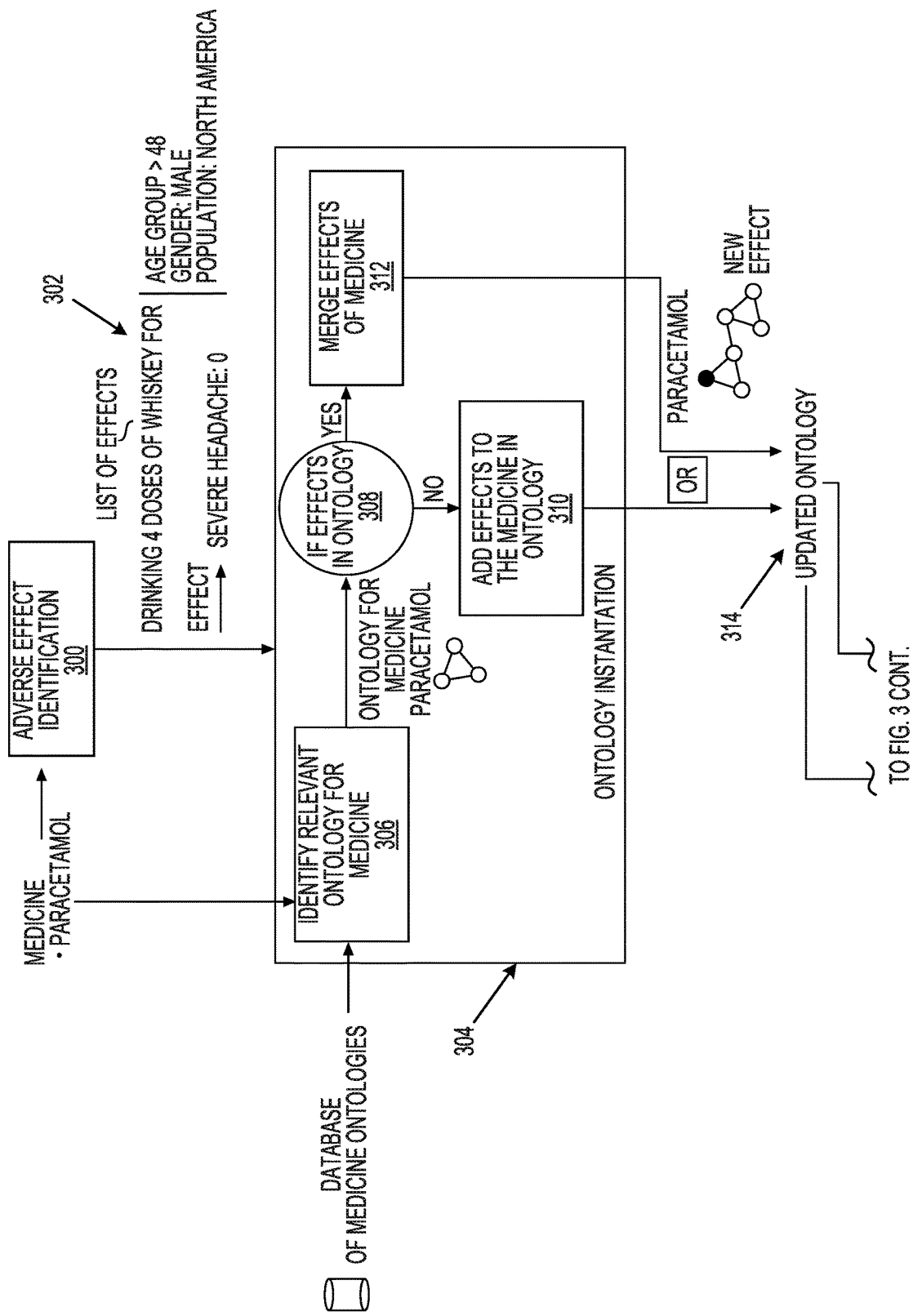
FIG. 3 illustrates further details of components of the adverse information based ontology reinforcement system of FIG. 1, and operation of the components of the adverse information based ontology reinforcement system of FIG. 1 with respect to a medical ontology, according to an example of the present disclosure.
Figure 3:
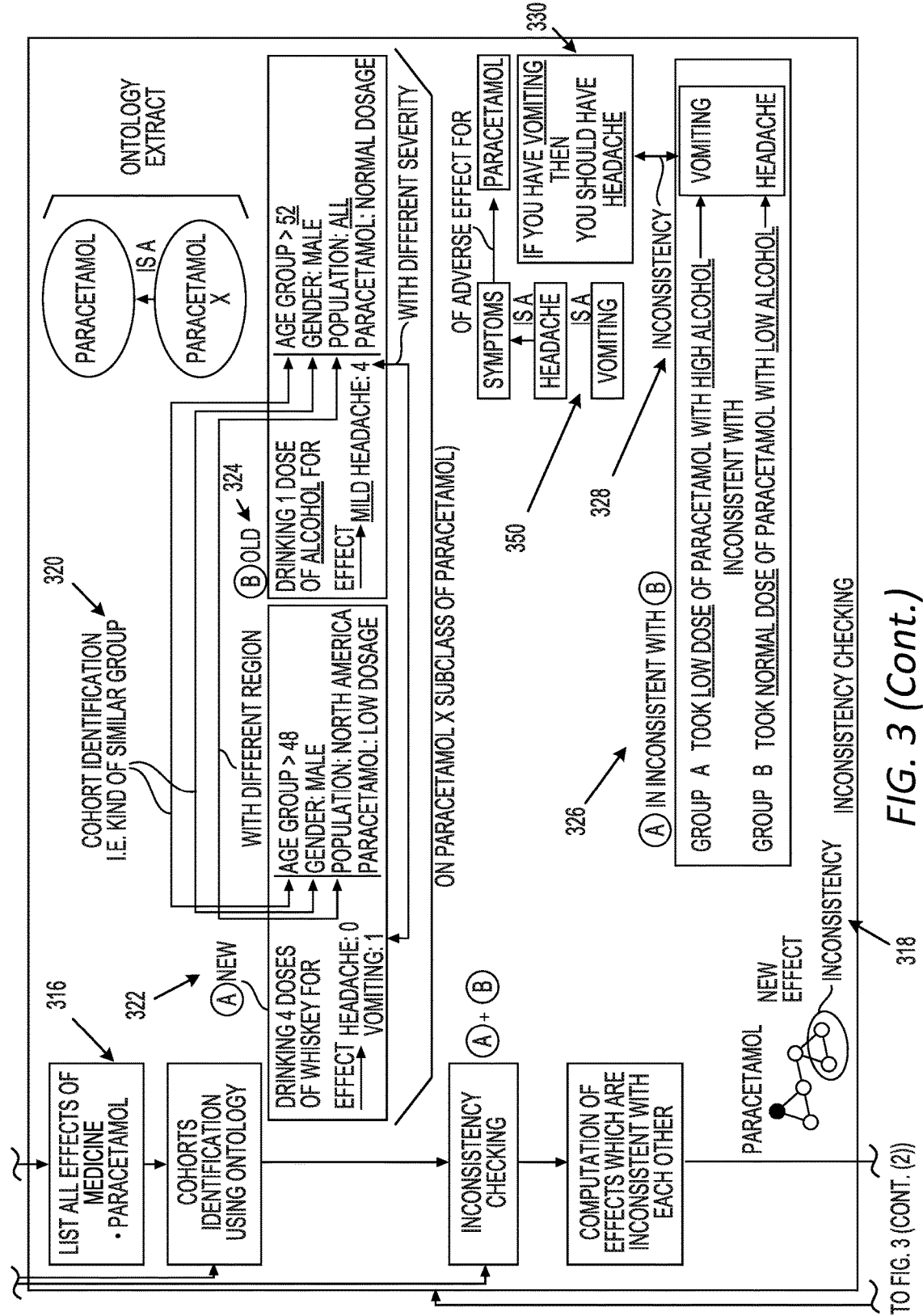

FIG. 3 illustrates further details of components of the system 100, and operation of the components of the system 100 with respect to a medical ontology, according to an example of the present disclosure.

At 300, the adverse information identifier 102 may ascertain, over a network 104, adverse information 106 related to a product 108 or a process 110. For the example of FIG. 3, in a similar manner as FIG. 2, the product 108 may include a medicine, and specifically, a paracetamol. For the example of FIG. 3, at 302, the adverse effect may include a severe headache level of zero (0) and vomiting after consuming four (4) doses of alcohol while also consuming paracetamol. Attributes such as age (e.g., 48), gender (e.g., male), and geographical location (e.g., North America) may also be identified in association with the adverse information 106.

At 304, generally, the ontology instantiator 112 may analyze the adverse information 106 related to the product 108 or the process 110.

At 306, the ontology instantiator 112 may identify, based on the adverse information 106 related to the product 108 or the process 110, a relevant ontology 114 of a plurality of ontologies 116. For example, the plurality of ontologies 116 may include medicine ontologies. Further, as per the example of FIG. 2, for FIG. 3, the relevant ontology 114 may include an ontology for the medicine paracetamol.

At 308, the ontology instantiator 112 may determine whether the adverse information 106 is present in the ascertained ontology 118.

At 310, based on a determination that the adverse information 106 is not present in the ascertained ontology 118, the ontology instantiator 112 may integrate the adverse information 106 into the ascertained ontology 118. For example, the ontology instantiator 112 may integrate the adverse information 106 into the ascertained ontology 118 by adding the adverse information 106 into the ascertained ontology 118 as new information.

At 312, based on a determination that the adverse information 106 is present in the ascertained ontology 118, the ontology instantiator 112 may merge the adverse information 106 into the ascertained ontology 118 with similar information present in the ascertained ontology 118. With respect to merging, the adverse information 106 may be concatenated with the similar information present in the ascertained ontology 118. For example, for an example of a medical ontology, effects of a medicine may be captured as adverse and similar effects under a same list. The merging may include concatenating the effects of the medicine in the list.

At 314, the ontology instantiator 112 may generate, based on the integrated adverse information, an updated ontology 120.

At 316, the inconsistency analyzer 122 may identify, in the updated ontology 120, similar existing information 124 corresponding to the ascertained adverse information 106. In this regard, the inconsistency analyzer 122 may capture all effects (e.g., output) of all similar medicines (e.g., of the input medicine paracetamol). With respect to the similar existing information 124, with respect to medicines, such information may be based on trials with different populations. For example, if Population 1 generates effects that include a severe headache level of zero after consuming alcohol while also consuming similar medicines, then the similar existing information 124 may include Population 2 and Population 3 in other trials that generate similar effects of a severe headache level of zero after consuming alcohol while also consuming similar medicines.

At 318, the inconsistency analyzer 122 may determine, based on an analysis of the identified similar existing information 124 and the ascertained adverse information 106, the inconsistency 126 between the identified similar existing information 124 and the ascertained adverse information 106. For example, assuming that an ontology includes knowledge that specifies that a low dose of paracetamol and high alcohol consumption should result in a headache and vomiting, a trial result that includes only vomiting after the use of paracetamol and alcohol may be considered as inconsistent with the knowledge in the ontology. In this regard, at 320, the inconsistency analyzer 122 may identify, based on the identified similar existing information 124 and the ascertained adverse information 106, cohorts 128 that are affected by the product 108 or the process 110 related to the ascertained adverse information 106. The inconsistency analyzer 122 may determine, based on the identified cohorts 128, a pair of cohorts that are inconsistent with each other. Thus, the inconsistency analyzer 122 may use the medicine ontology to identify similar and distinct clinical trials to identify cohorts that are affected by the medicine paracetamol. The medicine paracetamol ontology may drive the comparison of cases e.g., severity level, geo-location, etc. The output may include a set of pairs cases which are inconsistent with each other. For example, the pair of cohorts may include a first cohort (e.g., cohort "A") at 322 that includes the adverse effect of a severe headache level of zero (0) and vomiting after consuming four (4) doses of alcohol while also consuming a low dosage of paracetamol, and a second cohort (e.g., cohort "B") at 324 that includes the adverse effect of a moderate headache level of four (4) after consuming one (1) dose of alcohol while also consuming a normal dosage of paracetamol.

At 326, the inconsistency analyzer 122 may determine, based on the pair of cohorts that are inconsistent with each other, whether the inconsistency 126 exists between the identified similar existing information 124 and the ascertained adverse information 106. In this regard, at 328, the inconsistency 126 may indicate that taking a low dosage of paracetamol with high alcohol that results in vomiting only is inconsistent with taking a normal dosage of paracetamol with low alcohol resulting in a headache only. Thus, at 330, with respect to the inconsistency 126, if a user of the medicine paracetamol has vomiting, then the user should also have a headache.

Further, based on a determination that the inconsistency 126 exists between the identified similar existing information 124 and the ascertained adverse information 106, the inconsistency analyzer 122 may identify a root cause of the determined inconsistency 126. The root cause may represent the identification of knowledge which results in a contradiction, together with the history of trials that are used to derive the knowledge and the contexts of such trials.

At 332, the ontology reinforcer 130 may modify, based on the determined inconsistency 126 between the identified similar existing information 124 and the ascertained adverse information 106, the updated ontology 120 to generate, at 334, the reinforced ontology 132.

At 336, the ontology reinforcer 130 may modify, based on the determined inconsistency 126 between the identified similar existing information 124 and the ascertained adverse information 106, the updated ontology 120 to generate the reinforced ontology 132 by generating an inquiry 134 (shown as "input") that includes the determined inconsistency 126. The ontology reinforcer 130 may receive, based on the inquiry 134, a response 136 (e.g., with respect to the "input") that includes a confirmation of whether the determined inconsistency 126 is correct or incorrect. Based on the confirmation that the determined inconsistency 126 is incorrect, the ontology reinforcer 130 may remove the determined inconsistency 126 between the identified similar existing information 124 and the ascertained adverse information 106 to generate the reinforced ontology 132. That is, if the feedback with respect to the response 136 does not agree with the determined inconsistency 126, the axioms and/or knowledge that derive, infer, and/or materialize the determined inconsistency 126 may be removed.

At 338, based on the confirmation that the determined inconsistency 126 is correct, the ontology reinforcer 130 may generate a further inquiry 138 (e.g., shown as "explanation computation") that includes an explanation for the determined inconsistency.

At 340, the ontology reinforcer 130 may receive, based on the further inquiry 138, a further response 140 that includes a further confirmation of disagreement with the explanation for the determined inconsistency 126.

At 342, based on the further confirmation of the disagreement with the explanation for the determined inconsistency 126, the ontology reinforcer 130 may remove the determined inconsistency 126 between the identified similar existing information 124 and the ascertained adverse information 106 to generate the reinforced ontology 132. That is, if the feedback with respect to the explanation does not agree with the inconsistency, the axioms and/or knowledge that derive, infer, and/or materialize the inconsistency may be removed.

At 344, the ontology reinforcer 130 may receive, based on the further inquiry 138, the further response 140 that includes a further confirmation of agreement with the explanation for the determined inconsistency 126. That is, if the feedback agrees with the inconsistency, the rational and/or explanation behind the inconsistency may be determined. For example, any inconsistent axioms and/or knowledge in the medicine ontology may be highlighted. Based on the further confirmation of the agreement with the explanation for the determined inconsistency 126, the ontology reinforcer 130 may generate the reinforced ontology 132. In this regard, at 346, the ontology reinforcer 130 may ascertain, for the updated ontology 120, a link between a condition and a trigger related to the determined inconsistency 126. That is, the ontology reinforcer 130 may ascertain a link (or relation) between a condition and trigger (e.g., both in the ontology), which makes the ontology inconsistent) which is incorrect (e.g., due to the inconsistency). For example, a link may include a condition that includes a headache, and a trigger that includes a low dose of paracetamol.

At 348, the ontology reinforcer 130 may ascertain a policy 142 that is used to correct the link. The policy 142 may be used to correct the link (using the ontology and the relationship between the trigger and the condition). For example, the policy may indicate to optimize a distance between the trigger and the condition identified at 346. According to another example, the ascertained policy 142 may include removal of a link closest to one of the nodes of the ontology. Other policies may be utilized to correct the link. For example, other policies may include policies based on a distance between a trigger and a condition, a size of a trigger and a condition, similarity between a trigger and a condition, etc.

The ontology reinforcer 130 may assign a weight to each link of the updated ontology 120 according to the ascertained policy 142. That is, the ontology reinforcer 130 may implement a reward which is a function that weighs each link according to the policy. The reward may be used to compute an optimal solution with respect to the consistency of the ontology. For example, each link in an ontology may be assigned a weight based on a score (e.g., a score between 1-100) assigned by a policy. The weight may directly (e.g., one-to-one) correspond to the score, or may indirectly (e.g., a score of 10 may correspond to a weight of 1) to the score. In this regard, the policy may provide the framework to ascertain a weight value (e.g., a value between 1-10, 1-100, etc.). The weight value may then be used to "weigh" each link in the ontology.

The ontology reinforcer 130 may determine, based on the assigned weight to each link of the updated ontology 120 according to the ascertained policy 142, the reinforced ontology 132. In this regard, the ontology reinforcer 130 may identify a path between nodes associated with the determined inconsistency 126, where the path includes a plurality of links. The ontology reinforcer 130 may select, from the path, a link for removal based on the ascertained policy 142. For example, the link between headache and vomiting may be removed based on the inconsistency in the example case. Since this implication does not hold anymore, at 350, the "IS_A" relationship between headache and vomiting may be removed. The ontology reinforcer 130 may elaborate a links path between the two inconsistencies, where a path may be defined as a list of links between two nodes that create the inconsistency. Different metrics may be used to evaluate the length of a path. Examples of such metrics may include sum, average, weighted average, etc. For the metric that includes sum, the weight of each link in the path may be added to determine a final score. According to another example, with respect to average, the final score may be determined by averaging the weight of each link in the path. According to a further example, with respect to weighted average, the final score may be determined by weight averaging the weight of each link in the path. The ontology reinforcer 130 may remove links in the path by following the ascertained policy 142. For example, as disclosed herein, the ascertained policy 142 may prioritize the removal of links closer to one of two nodes (e.g., one of the two inconsistencies). Alternatively or additionally, as disclosed herein, a policy may prioritize to remove links not in the path anywhere in the ontology. In this regard, a path in the ontology that includes the highest score (or weight) may be retained, and any path below a specified threshold (that may be based on sum, average, weighted average, etc.) may be removed.

The ontology reinforcer 130 may utilize the assigned weight for each link to determine an overall score 144 based on the removal of the selected link. For example, the overall score 144 may be determined as a weighted average of each link weight, for example, by summing all weights of all links, and averaging the results of the summation.

The ontology reinforcer 130 may determine whether the removal of the selected link results in a lowest overall score compared to removal of another link of the path. Based on a determination that the removal of the selected link results in the lowest overall score, the ontology reinforcer 130 may remove the selected link. That is, as many candidate links may be selected for removal, and a reward function may be used to evaluate the impact of removing a link from the ontology. This reward function may evaluate the overall score of the ontology after removal of the link. The link resulting to the lowest overall reward score may be removed from the ontology.

Further, the ontology reinforcer 130 may determine the reinforced ontology 132 by removing the determined inconsistency 126 based on the removal of the selected link that results in the lowest overall score.

At 352, the aforementioned steps with respect to removal of the appropriate link may be iterated until the determined inconsistency 126 (and any further cascading inconsistencies) is removed while optimizing the overall reward function for the ontology. In this regard, removal of a link and/or node in an ontology may generate other inconsistencies, and thus, such cascading inconsistencies may need to be addressed based on the removal of other links and/or nodes by the iteration operation at 352.

Figure 4:
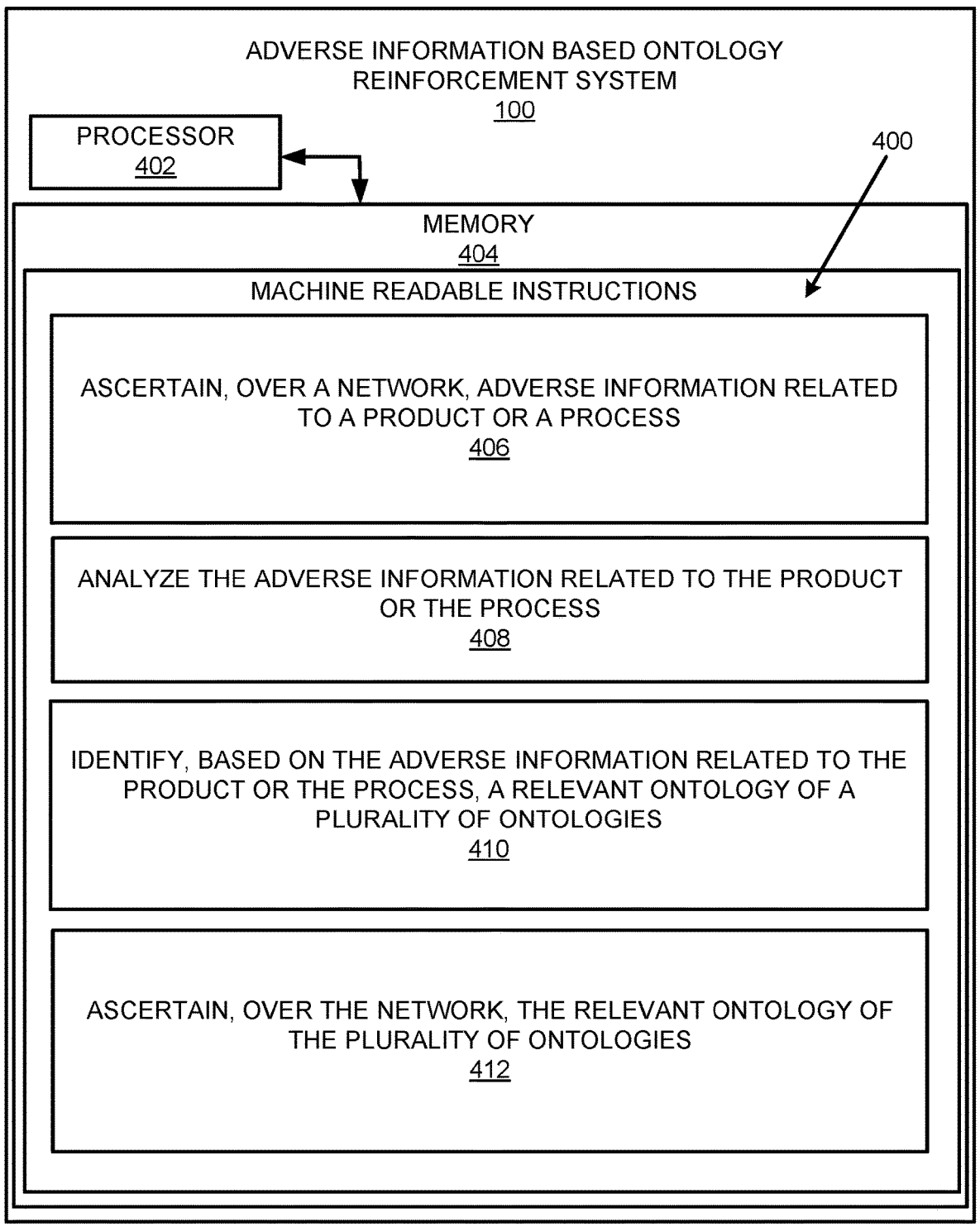
FIG. 4 illustrates a block diagram for adverse information based ontology reinforcement, according to an example of the present disclosure.
Figure 4:
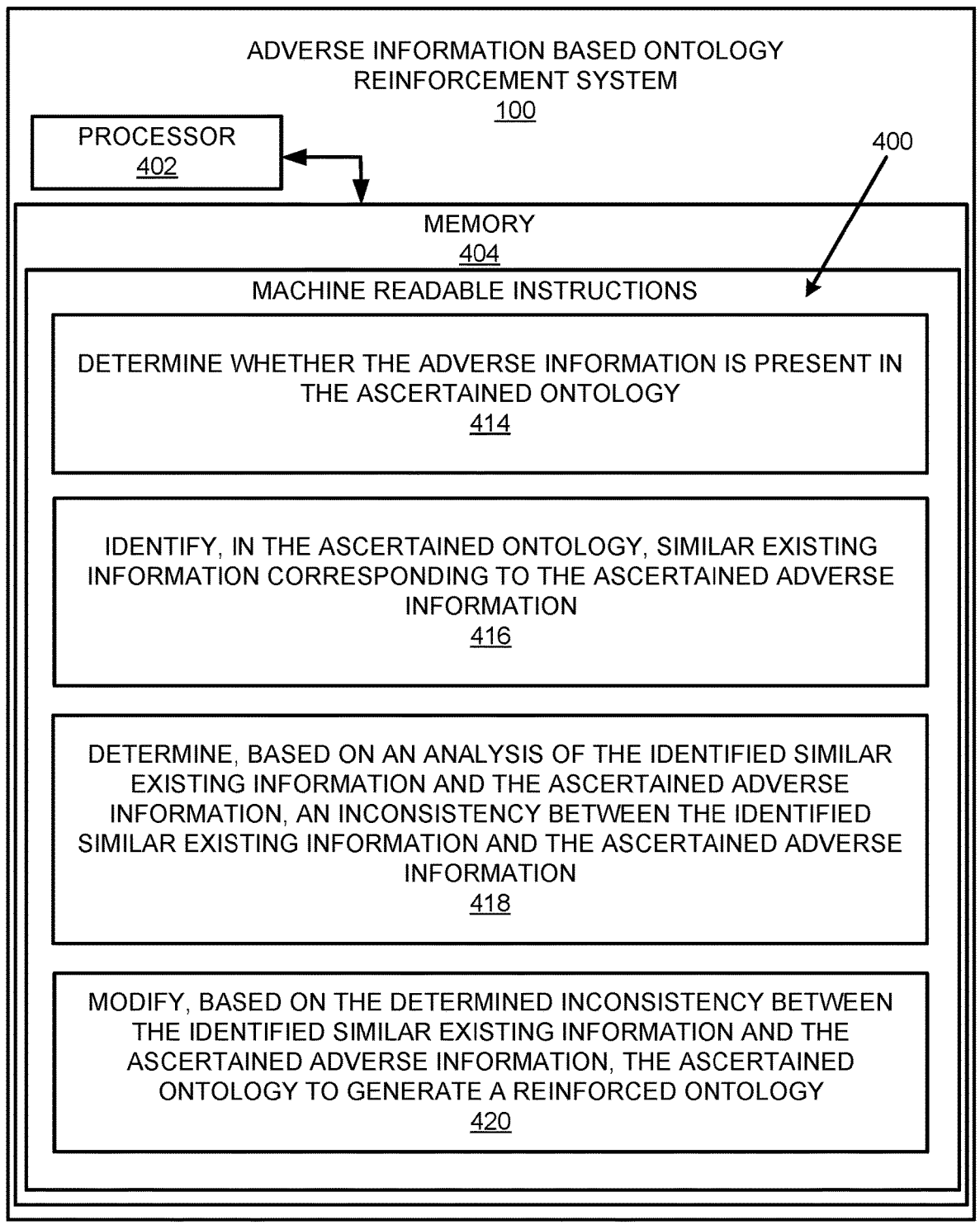
Figure 6:
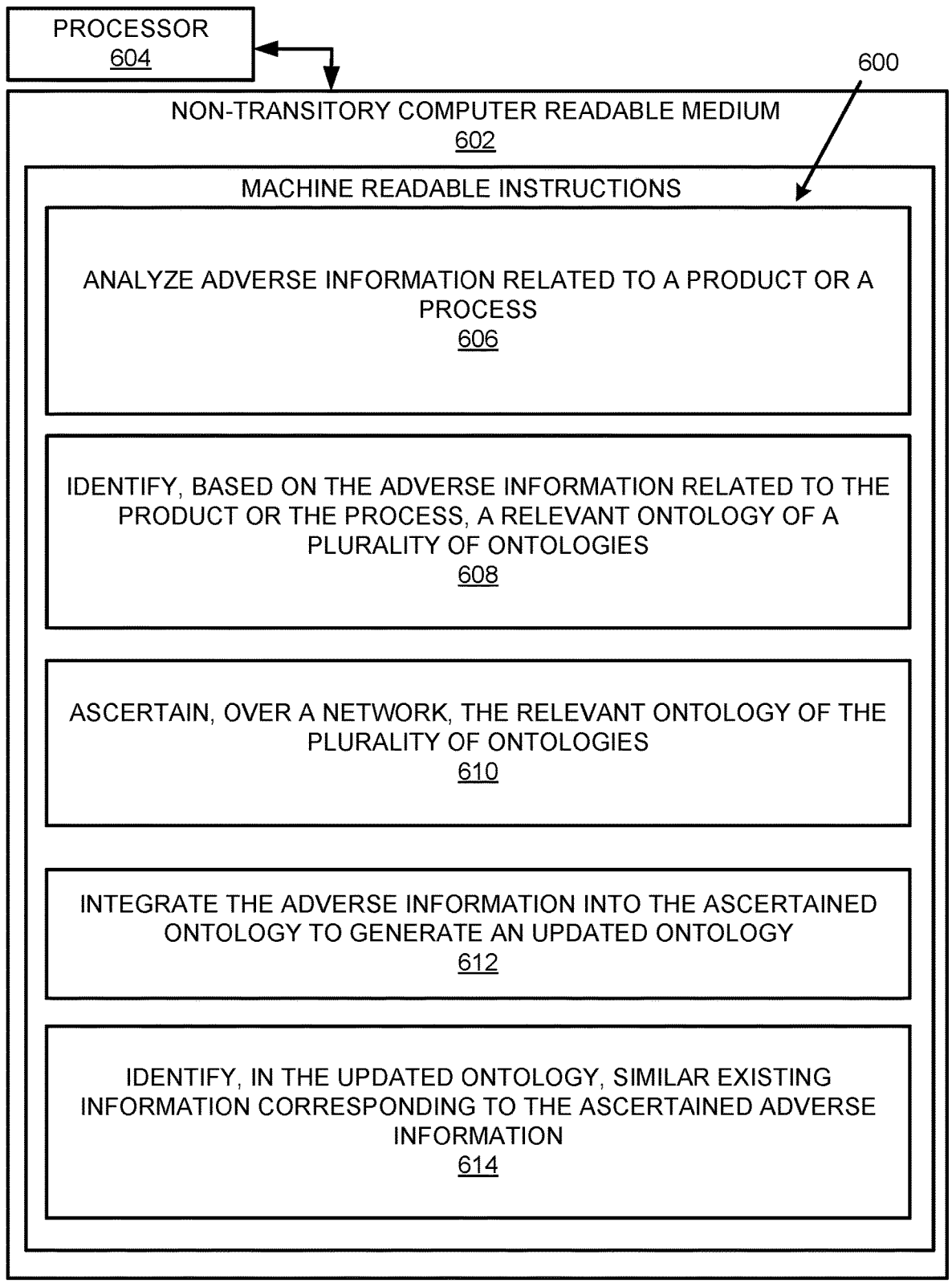
FIG. 6 illustrates a further block diagram for adverse information based ontology reinforcement, according to an example of the present disclosure.
Figure 6:
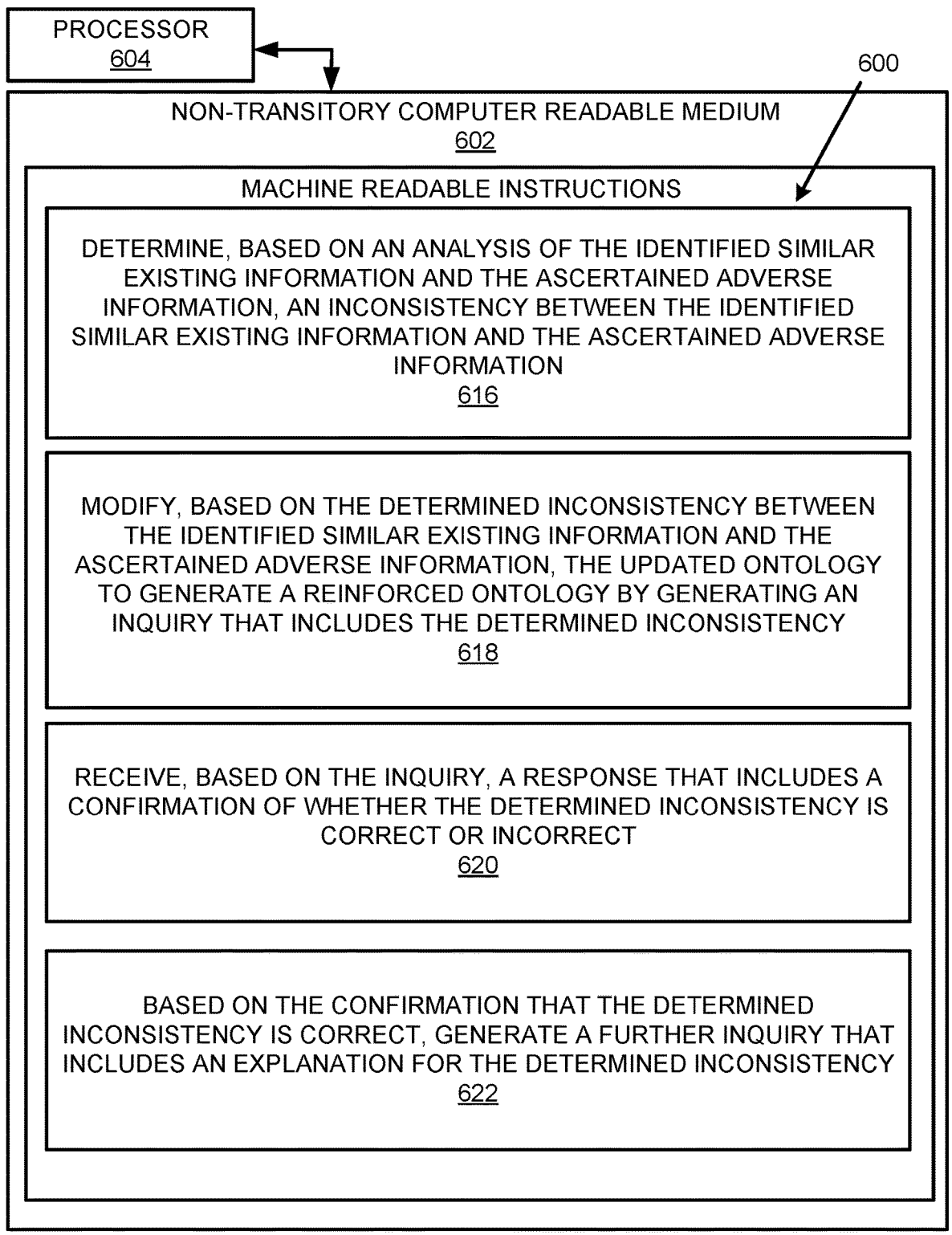
Figure 6:
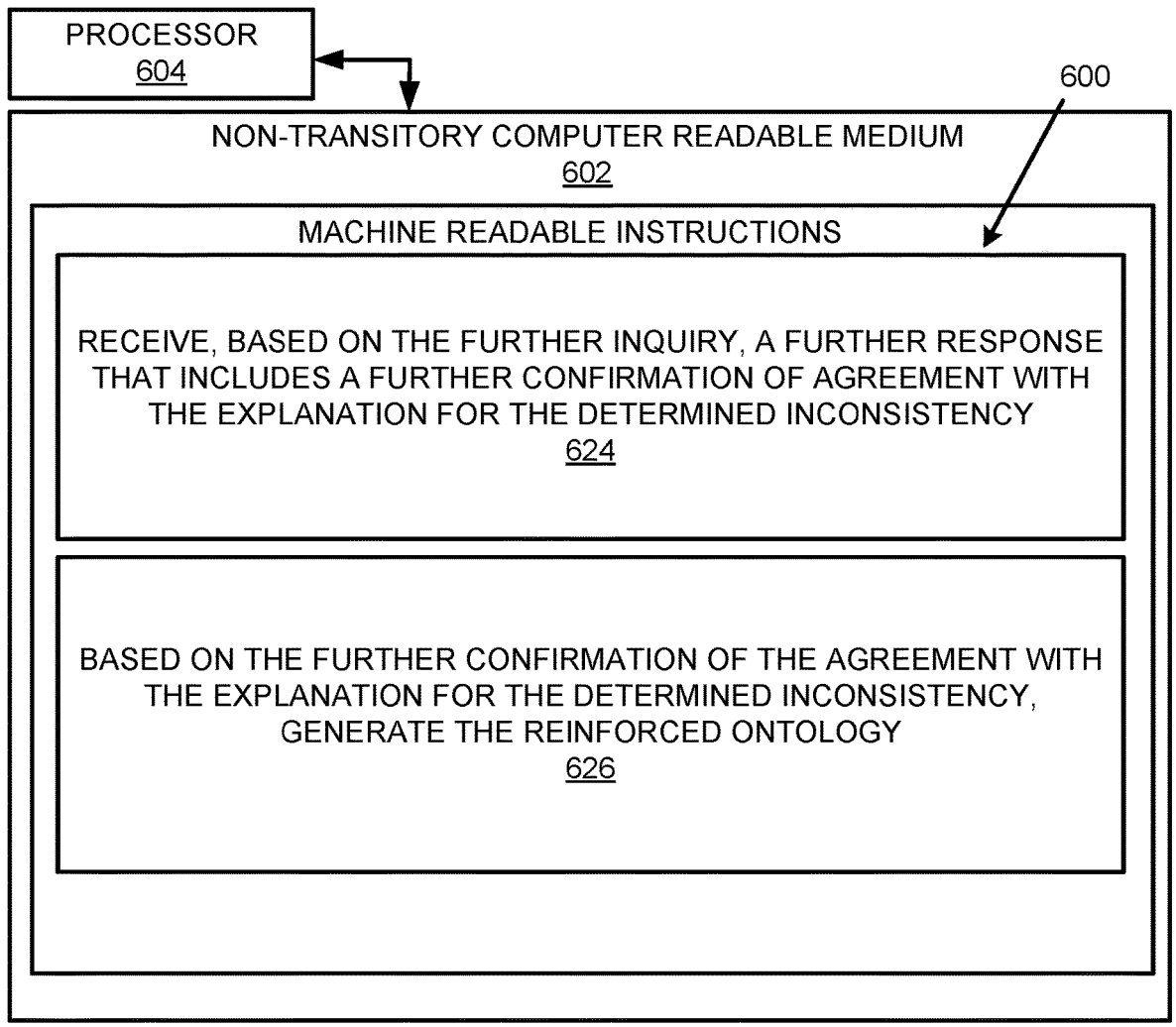

FIGS. 4-6 respectively illustrate a block diagram 400, a flowchart of a method 500, and a further block diagram 600 for adverse information based ontology reinforcement, according to examples. The block diagram 400, the method 500, and the block diagram 600 may be implemented on the system 100 described above with reference to FIG. 1 by way of example and not limitation. The block diagram 400, the method 500, and the block diagram 600 may be practiced in other systems. In addition to showing the block diagram 400, FIG. 4 shows hardware of the system 100 that may execute the instructions of the block diagram 400. The hardware may include a processor 402, and a memory 404 storing machine readable instructions that when executed by the processor cause the processor to perform the instructions of the block diagram 400. The memory 404 may represent a non-transitory computer readable medium. FIG. 5 may represent a method for adverse information based ontology reinforcement, and the steps of the method. FIG. 6 may represent a non-transitory computer readable medium 602 having stored thereon machine readable instructions to provide an adverse information based ontology reinforcement. The machine readable instructions, when executed, cause a processor 604 to perform the instructions of the block diagram 600 also shown in FIG. 6.

The processor 402 of FIG. 4 and/or the processor 604 of FIG. 6 may include a single or multiple processors or other hardware processing circuit, to execute the methods, functions and other processes described herein. These methods, functions and other processes may be embodied as machine readable instructions stored on a computer readable medium, which may be non-transitory (e.g., the non-transitory computer readable medium 602 of FIG. 6), such as hardware storage devices (e.g., RAM (random access memory), ROM (read only memory), EPROM (erasable, programmable ROM), EEPROM (electrically erasable, programmable ROM), hard drives, and flash memory). The memory 404 may include a RAM, where the machine readable instructions and data for a processor may reside during runtime.

Referring to FIGS. 1-4, and particularly to the block diagram 400 shown in FIG. 4, the memory 404 may include instructions 406 to ascertain, over a network 104, adverse information 106 related to a product 108 or a process 110.

The processor 402 may fetch, decode, and execute the instructions 408 to analyze the adverse information 106 related to the product 108 or the process 110.

The processor 402 may fetch, decode, and execute the instructions 410 to identify, based on the adverse information 106 related to the product 108 or the process 110, a relevant ontology 114 of a plurality of ontologies 116.

The processor 402 may fetch, decode, and execute the instructions 412 to ascertain, over the network 104, the relevant ontology 114 of the plurality of ontologies 116. The relevant ontology 114 may be designated an ascertained ontology 118.

The processor 402 may fetch, decode, and execute the instructions 414 to determine whether the adverse information 106 is present in the ascertained ontology 118.

The processor 402 may fetch, decode, and execute the instructions 416 to identify, in the ascertained ontology, similar existing information 124 corresponding to the ascertained adverse information 106.

The processor 402 may fetch, decode, and execute the instructions 418 to determine, based on an analysis of the identified similar existing information 124 and the ascertained adverse information 106, an inconsistency 126 between the identified similar existing information 124 and the ascertained adverse information 106.

The processor 402 may fetch, decode, and execute the instructions 420 to modify, based on the determined inconsistency 126 between the identified similar existing information 124 and the ascertained adverse information 106, the ascertained ontology to generate a reinforced ontology 132.

Referring to FIGS. 1-3 and 5, and particularly FIG. 5, for the method 500, at block 502, the method may include analyzing adverse information 106 related to a product 108 or a process 110.

At block 504, the method may include identifying, based on the adverse information 106 related to the product 108 or the process 110, a relevant ontology 114 of a plurality of ontologies 116.

At block 506, the method may include ascertaining, over a network 104, the relevant ontology 114 of the plurality of ontologies 116. The relevant ontology 114 may be designated an ascertained ontology 118.

At block 508, the method may include determining whether the adverse information 106 is present in the ascertained ontology 118.

At block 510, based on a determination that the adverse information 106 is present in the ascertained ontology 118, the method may include merging the adverse information 106 into the ascertained ontology 118 with similar information present in the ascertained ontology 118.

At block 512, based on a determination that the adverse information 106 is not present in the ascertained ontology 118, the method may include adding the adverse information 106 into the ascertained ontology 118 as new information.

At block 514, the method may include generating, based on the merged or added adverse information 106, an updated ontology 120.

At block 516, the method may include identifying, in the updated ontology 120, similar existing information 124 corresponding to the ascertained adverse information 106.

At block 518, the method may include determining, based on an analysis of the identified similar existing information 124 and the ascertained adverse information 106, an inconsistency 126 between the identified similar existing information 124 and the ascertained adverse information 106.

At block 520, the method may include modifying, based on the determined inconsistency 126 between the identified similar existing information 124 and the ascertained adverse information 106, the updated ontology 120 to generate a reinforced ontology 132.

Referring to FIGS. 1-10 and 6, and particularly FIG. 6, for the block diagram 600, the non-transitory computer readable medium 602 may include instructions 606 to analyze adverse information 106 related to a product 108 or a process 110.

The processor 604 may fetch, decode, and execute the instructions 608 to identify, based on the adverse information 106 related to the product 108 or the process 110, a relevant ontology 114 of a plurality of ontologies 116.

The processor 604 may fetch, decode, and execute the instructions 610 to ascertain, over a network 104, the relevant ontology 114 of the plurality of ontologies 116. The relevant ontology 114 may be designated an ascertained ontology 118.

The processor 604 may fetch, decode, and execute the instructions 612 to integrate the adverse information 106 into the ascertained ontology 118 to generate an updated ontology 120.

The processor 604 may fetch, decode, and execute the instructions 614 to identify, in the updated ontology 120, similar existing information 124 corresponding to the ascertained adverse information 106.

The processor 604 may fetch, decode, and execute the instructions 616 to determine, based on an analysis of the identified similar existing information 124 and the ascertained adverse information 106, an inconsistency 126 between the identified similar existing information 124 and the ascertained adverse information 106.

The processor 604 may fetch, decode, and execute the instructions 618 to modify, based on the determined inconsistency 126 between the identified similar existing information 124 and the ascertained adverse information 106, the updated ontology 120 to generate a reinforced ontology 132 by generating an inquiry that includes the determined inconsistency 126.

The processor 604 may fetch, decode, and execute the instructions 620 to receive, based on the inquiry, a response that includes a confirmation of whether the determined inconsistency 126 is correct or incorrect.

Based on the confirmation that the determined inconsistency 126 is correct, the processor 604 may fetch, decode, and execute the instructions 622 to generate a further inquiry that includes an explanation for the determined inconsistency 126.

The processor 604 may fetch, decode, and execute the instructions 624 to receive, based on the further inquiry, a further response that includes a further confirmation of agreement with the explanation for the determined inconsistency 126.

Based on the further confirmation of the agreement with the explanation for the determined inconsistency 126, the processor 604 may fetch, decode, and execute the instructions 626 to generate the reinforced ontology 132.

What has been described and illustrated herein is an example along with some of its variations. The terms, descriptions and figures used herein are set forth by way of illustration only and are not meant as limitations. Many variations are possible within the spirit and scope of the subject matter, which is intended to be defined by the following claims—and their equivalents—in which all terms are meant in their broadest reasonable sense unless otherwise indicated.

What is claimed is:

1. A system comprising:
   an adverse information identifier, executed by at least one hardware processor, to ascertain, over a network, adverse information related to a product or a process;
   an ontology instantiator, executed by the at least one hardware processor, to
      analyze the adverse information related to the product or the process,
      identify, based on the adverse information related to the product or the process, a relevant ontology of a plurality of ontologies,
      ascertain, over the network, the relevant ontology of the plurality of ontologies, wherein the relevant ontology is designated an ascertained ontology,
      determine whether the adverse information is present in the ascertained ontology,
      integrate, based on a determination that the adverse information is not present in the ascertained ontology, the adverse information into the ascertained ontology, and
      generate, based on the integrated adverse information, an updated ontology;
   an inconsistency analyzer, executed by the at least one hardware processor, to
      identify, in the updated ontology, similar existing information corresponding to the ascertained adverse information, and
      determine, based on an analysis of the identified similar existing information and the ascertained adverse information, an inconsistency between the identified similar existing information and the ascertained adverse information; and
   an ontology reinforcer, executed by the at least one hardware processor, to
      modify, based on the determined inconsistency between the identified similar existing information and the ascertained adverse information, the updated ontology to generate a reinforced ontology.

2. The system according to claim 1, wherein the adverse information includes an adverse effect related to a product that includes a medical drug.

3. The system according to claim 1, wherein the ontology instantiator is to identify, based on the adverse information related to the product or the process, the relevant ontology of the plurality of ontologies by:
   receiving the plurality of ontologies; and
   identifying, based on the adverse information related to the product or the process, the relevant ontology of the received plurality of ontologies.

4. The system according to claim 1, wherein the inconsistency analyzer is to determine, based on the analysis of the identified similar existing information and the ascertained adverse information, the inconsistency between the identified similar existing information and the ascertained adverse information by:
   identifying, based on the identified similar existing information and the ascertained adverse information, cohorts that are affected by the product or the process related to the ascertained adverse information;
   determining, based on the identified cohorts, a pair of cohorts that are inconsistent with each other;
   determining, based on the pair of cohorts that are inconsistent with each other, whether the inconsistency exists between the identified similar existing information and the ascertained adverse information; and
   based on a determination that the inconsistency exists between the identified similar existing information and the ascertained adverse information, identifying a root cause of the determined inconsistency.

5. The system according to claim 1, wherein the ontology reinforcer is to modify, based on the determined inconsistency between the identified similar existing information and the ascertained adverse information, the updated ontology to generate the reinforced ontology by:
   generating an inquiry that includes the determined inconsistency;
   receiving, based on the inquiry, a response that includes a confirmation of whether the determined inconsistency is correct or incorrect; and
   based on the confirmation that the determined inconsistency is incorrect, removing the determined inconsistency between the identified similar existing information and the ascertained adverse information to generate the reinforced ontology.

6. The system according to claim 1, wherein the ontology reinforcer is to modify, based on the determined inconsistency between the identified similar existing information and the ascertained adverse information, the updated ontology to generate the reinforced ontology by:
   generating an inquiry that includes the determined inconsistency;
   receiving, based on the inquiry, a response that includes a confirmation of whether the determined inconsistency is correct or incorrect;

based on the confirmation that the determined inconsistency is correct, generating a further inquiry that includes an explanation for the determined inconsistency;

receiving, based on the further inquiry, a further response that includes a further confirmation of disagreement with the explanation for the determined inconsistency; and based on the further confirmation of the disagreement with the explanation for the determined inconsistency, removing the determined inconsistency between the identified similar existing information and the ascertained adverse information to generate the reinforced ontology.

7. The system according to claim 1, wherein the ontology reinforcer is to modify, based on the determined inconsistency between the identified similar existing information and the ascertained adverse information, the updated ontology to generate the reinforced ontology by:

generating an inquiry that includes the determined inconsistency;

receiving, based on the inquiry, a response that includes a confirmation of whether the determined inconsistency is correct or incorrect;

based on the confirmation that the determined inconsistency is correct, generating a further inquiry that includes an explanation for the determined inconsistency;

receiving, based on the further inquiry, a further response that includes a further confirmation of agreement with the explanation for the determined inconsistency; and based on the further confirmation of the agreement with the explanation for the determined inconsistency, generating the reinforced ontology.

8. The system according to claim 7, wherein the ontology reinforcer is to generate, based on the further confirmation of the agreement with the explanation for the determined inconsistency, the reinforced ontology by:

ascertaining, for the updated ontology, a link between a condition and a trigger related to the determined inconsistency;

ascertaining a policy that is used to correct the link;

assigning a weight to each link of the updated ontology according to the ascertained policy; and determining, based on the assigned weight to each link of the updated ontology according to the ascertained policy, the reinforced ontology.

9. The system according to claim 8, wherein the ontology reinforcer is to determine, based on the assigned weight to each link of the updated ontology according to the ascertained policy, the reinforced ontology by:

identifying a path between nodes associated with the determined inconsistency, wherein the path includes a plurality of links;

selecting, from the path, a link for removal based on the ascertained policy;

utilizing the assigned weight for each link to determine an overall score based on the removal of the selected link;

determining whether the removal of the selected link results in a lowest overall score compared to removal of another link of the path;

based on a determination that the removal of the selected link results in the lowest overall score, removing the selected link; and determining the reinforced ontology by removing the determined inconsistency based on the removal of the selected link that results in the lowest overall score.

10. The system according to claim 9, wherein the ascertained policy includes removal of a link closest to one of the nodes.

11. A computer implemented method comprising:

analyzing adverse information related to a product or a process;

identifying, based on the adverse information related to the product or the process, a relevant ontology of a plurality of ontologies;

ascertaining, over a network, the relevant ontology of the plurality of ontologies, wherein the relevant ontology is designated an ascertained ontology;

determining whether the adverse information is present in the ascertained ontology;

based on a determination that the adverse information is present in the ascertained ontology, merging the adverse information into the ascertained ontology with similar information present in the ascertained ontology;

based on a determination that the adverse information is not present in the ascertained ontology, adding the adverse information into the ascertained ontology as new information;

generating, based on the merged or added adverse information, an updated ontology;

identifying, in the updated ontology, similar existing information corresponding to the ascertained adverse information;

determining, based on an analysis of the identified similar existing information and the ascertained adverse information, an inconsistency between the identified similar existing information and the ascertained adverse information; and modifying, based on the determined inconsistency between the identified similar existing information and the ascertained adverse information, the updated ontology to generate a reinforced ontology.

12. The method according to claim 11, wherein the adverse information includes an adverse effect related to a product that includes a medical drug.

13. The method according to claim 11, further comprising:

generating an output that includes the reinforced ontology; and transmitting, over the network, the reinforced ontology for storage in a database that includes the plurality of ontologies.

14. The method according to claim 11, wherein determining, based on the analysis of the identified similar existing information and the ascertained adverse information, the inconsistency between the identified similar existing information and the ascertained adverse information further comprises:

identifying, based on the identified similar existing information and the ascertained adverse information, cohorts that are affected by the product or the process related to the ascertained adverse information;

determining, based on the identified cohorts, a pair of cohorts that are inconsistent with each other;

determining, based on the pair of cohorts that are inconsistent with each other, whether the inconsistency exists between the identified similar existing information and the ascertained adverse information; and based on a determination that the inconsistency exists between the identified similar existing information and the ascertained adverse information, identifying a root cause of the determined inconsistency.

15. The method according to claim 11, wherein modifying, based on the determined inconsistency between the identified similar existing information and the ascertained adverse information, the updated ontology to generate the reinforced ontology further comprises:
- generating an inquiry that includes the determined inconsistency;
- receiving, based on the inquiry, a response that includes a confirmation of whether the determined inconsistency is correct or incorrect; and
- based on the confirmation that the determined inconsistency is incorrect, removing the determined inconsistency between the identified similar existing information and the ascertained adverse information to generate the reinforced ontology.

16. The method according to claim 11, wherein modifying, based on the determined inconsistency between the identified similar existing information and the ascertained adverse information, the updated ontology to generate the reinforced ontology further comprises:
- generating an inquiry that includes the determined inconsistency;
- receiving, based on the inquiry, a response that includes a confirmation of whether the determined inconsistency is correct or incorrect;
- based on the confirmation that the determined inconsistency is correct, generating a further inquiry that includes an explanation for the determined inconsistency;
- receiving, based on the further inquiry, a further response that includes a further confirmation of disagreement with the explanation for the determined inconsistency; and
- based on the further confirmation of the disagreement with the explanation for the determined inconsistency, removing the determined inconsistency between the identified similar existing information and the ascertained adverse information to generate the reinforced ontology.

17. A non-transitory computer readable medium having stored thereon machine readable instructions, the machine readable instructions, when executed, cause at least one hardware processor to:
- analyze adverse information related to a product or a process;
- identify, based on the adverse information related to the product or the process, a relevant ontology of a plurality of ontologies;
- ascertain, over a network, the relevant ontology of the plurality of ontologies, wherein the relevant ontology is designated an ascertained ontology;
- integrate the adverse information into the ascertained ontology to generate an updated ontology;
- identify, in the updated ontology, similar existing information corresponding to the ascertained adverse information;
- determine, based on an analysis of the identified similar existing information and the ascertained adverse information, an inconsistency between the identified similar existing information and the ascertained adverse information; and
- modify, based on the determined inconsistency between the identified similar existing information and the ascertained adverse information, the updated ontology to generate a reinforced ontology by
  - generating an inquiry that includes the determined inconsistency,
  - receiving, based on the inquiry, a response that includes a confirmation of whether the determined inconsistency is correct or incorrect,
  - based on the confirmation that the determined inconsistency is correct, generating a further inquiry that includes an explanation for the determined inconsistency,
  - receiving, based on the further inquiry, a further response that includes a further confirmation of agreement with the explanation for the determined inconsistency, and
  - based on the further confirmation of the agreement with the explanation for the determined inconsistency, generating the reinforced ontology.

18. The non-transitory computer readable medium according to claim 17, wherein the machine readable instructions to generate, based on the further confirmation of the agreement with the explanation for the determined inconsistency, the reinforced ontology, when executed by the at least one hardware processor further cause the at least one hardware processor to:
- ascertain, for the updated ontology, a link between a condition and a trigger related to the determined inconsistency;
- ascertain a policy that is used to correct the link;
- assign a weight to each link of the updated ontology according to the ascertained policy; and
- determine, based on the assigned weight to each link of the updated ontology according to the ascertained policy, the reinforced ontology.

19. The non-transitory computer readable medium according to claim 18, wherein the machine readable instructions to determine, based on the assigned weight to each link of the updated ontology according to the ascertained policy, the reinforced ontology, when executed by the at least one hardware processor further cause the at least one hardware processor to:
- identify a path between nodes associated with the determined inconsistency, wherein the path includes a plurality of links;
- select, from the path, a link for removal based on the ascertained policy;
- utilize the assigned weight for each link to determine an overall score based on the removal of the selected link;
- determine whether the removal of the selected link results in a lowest overall score compared to removal of another link of the path;
- based on a determination that the removal of the selected link results in the lowest overall score, remove the selected link; and
- determine the reinforced ontology by removing the determined inconsistency based on the removal of the selected link that results in the lowest overall score.

* * * * *